US00PP08994P

United States Patent [19]

Machin

[11] Patent Number: Plant 8,994

[45] Date of Patent: Nov. 29, 1994

[54] CHRYSANTHEMUM PLANT NAMED MAJESTY

[75] Inventor: Barrie J. Machin, Hants, England

[73] Assignee: Goldstock Breeding Limited, Hants, England

[21] Appl. No.: 139,009

[22] Filed: Oct. 21, 1993

[51] Int. Cl.[5] ..... A01H 5/00

[52] U.S. Cl. ..... Plt./82.4

[58] Field of Search ..... Plt. 74.1, 82.4

*Primary Examiner*—Howard J. Locker

*Attorney, Agent, or Firm*—Foley & Lardner

[57] ABSTRACT

A new Chrysanthemum cultivar named Majesty, characterized by the combined features of flat capitulum form, daisy capitulum type, light pink ray floret color, capitulum diameter of 80–90 cm, a response period of 59–63 days, a plant height of 91–102 cm when grown with 14 long days prior to start of short days, and inverted pyramid flower formation.

4 Drawing Sheets

The present invention comprises a new and distinct cultivar of Chrysanthemum, botanically known as *Dendranthema grandiflora*, and referred to by the cultivar name Majesty.

Majesty was originated from a cross made by the inventor, Barrie J. Machin, in a controlled breeding program in Fareham, England in 1986.

The female parent of Majesty was a seedling known as Sugar, disclosed in U.S. Plant Pat. No. 3,776, and described as a cut spray single mum daisy type having a pink ray floret color, a diameter of capitulum of 76 to 86 mm when fully open, a flowering response to short days of 61–63 days, a plant height of 86–96 cm when grown with 14 long days prior to start of short days, a peduncle length of the first lateral of 8 to 15 cm and of the fourth lateral of 15–20 cm, and a terminal spray formation. The above characteristics are based on plants grown in Fareham, England.

The male parent of Majesty was a seedling identified as Delta, disclosed in Plant Pat. No. 5,815, and described as a single mum daisy type having a pink ray floret color, diameter of capitulum of 80 mm, a flowering response of 63 days, a plant height of 90 cm when grown with 14 long days prior to start of short days, a peduncle length of the first lateral of 8 cm and of the fourth lateral of 12 cm, and a flat on inverted triangle spray formation. The above characteristics are based on plants grown in Fareham, England.

Majesty was discovered and selected as one flowering plant within the progeny of the stated cross by Barrie J. Machin in March 1986 in a controlled environment in Fareham, England.

The first act of asexual reproduction of Majesty was accomplished when vegetative cuttings were taken from the initial selection in June 1986 in a controlled environment in Fareham, England by Barrie J. Machin.

Horticultural examination of controlled flowerings of successive plantings has shown that the unique combination of characteristics as herein disclosed for Majesty are firmly fixed and are retained through successive generations of asexual reproduction.

Majesty has not been observed under all possible environmental conditions. The phenotype may vary somewhat with variations in environment such as temperature, light intensity and daylength, without, however, any variance in genotype.

The following observations, measurements and comparisons describe plants grown in Fareham, England under greenhouse conditions which approximate those generally used in commercial greenhouse practice.

The following traits have been repeatedly observed and are determined to be basic characteristics of Majesty, which, in combination, distinguish this Chrysanthemum as a new and distinct cultivar:

1. Flat capitulum form.
2. Daisy capitulum type.
3. Light pink ray floret color.
4. Diameter across face of capitulum of 80–90 mm when fully opened.
5. Flowering response under normal temperatures is 59 to 63 days after start of short days.
6. Plant height is 91 to 102 cm when grown with 14 long days prior to start of short days.
7. Peduncle length of the first lateral at flowering after removing the apical bud and without growth regulator applications is 9.5 cm; peduncle length of the fourth lateral at flowering is 12.5 cm.
8. Flower formation is at approximately the same height since lower laterals are longer than upper laterals. This gives the effect of an inverted pyramid shape.

The accompanying photographic drawings show typical inflorescence and leaf characteristics of Majesty, with the colors being as nearly true as possible with illustrations of this type.

Sheet 1 is a color photograph of Majesty grown as a single stem spray cut mum.

Sheet 2 and 3 are black and white photographs showing the upper and under sides respectively of the leaves of Majesty in three stages of development (mature, intermediate and immature).

Sheet 4 is a black and white photograph showing three views of the inflorescence of Majesty.

Of the commercial cultivars known to the inventor, the most similar in comparison to Majesty is the commercially well-known cultivar identified as Pink Marble. Reference is made to attached Chart A, which compares certain characteristics of Majesty with the same characteristics of Pink Marble. Similar traits are capitulum form, type and diameter, response, and spray formation. The ray floret color of both cultivars is described as pink, but Majesty is a deeper pink color than Pink Marble. Further, plant height and length of laterals is substantially less for Majesty.

In the following description, color references are made to The Royal Horticultural Society Colour Chart.

The color values were determined on plant material grown as a single spray cut mum in Fareham, England in June 1986.

Classification:

*Botanical.*—*Dendranthema grandiflora* cv Majesty.

*Commercial.*—Daisy spray cut mum.

INFLORESCENCE

A. Capitulum:

*Form.*—Flat.

*Type.*—Daisy.

*Diameter across face.*—80–90 mm.

B. Corolla of ray florets:

*Color (general tonality from a distance of three meters).*—Pink.

*Color (upper surface).*—56A.

*Color (under surface).*—56C.

*Shape.*—Curving and pointed.

*Quantity.*—Approximately 20 per flower arranged in two layers.

C. Disc florets:

*Diameter.*—12–17 mm.

*Color.*—Immature, 143C; mature, 13A.

*Quantity.*—Approximately 200 per flower.

D. Reproductive organs:

*Androecium.*—Present on ray florets; very small quantity of pollen.

*Gynoecium.*—Present on disc and ray florets.

PLANT

A. General appearance:

*Height.*—91–102 cm.

B. Foliage:

*Color (upper surface).*—137B.

*Color (under surface).*—137C.

*Shape.*—Five (5) main lobes, broadly toothed, typically 6–8 teeth per lobe; teeth taper to a point. See photos.

C. Habit: Regular branching habit, typically one branch developing per leaf axil; flowers are produced at the top of the inflorescence which typically contains 8–10 flowers; flower pedicels are at angles of 45° or less to the stems.

CHART A

COMPARISONS MADE OF PLANTS GROWN AS SINGLE STEM SPRAY CUT MUMS IN FAREHAM, ENGLAND

| CHARACTERISTICS | MAJESTY | PINK MARBLE |
|---|---|---|
| Ray floret color | Pink | Pink |
| Capitulum form and type | Flat Daisy | Flat Daisy |
| Diameter across face of capitulum | 80 to 90 mm | 80 to 90 mm |
| Flowering Response | 59 to 63 days | 56 to 63 days |
| Plant height | 91 to 102 cm | 111 to 120 cm |
| Peduncle length: | | |
| 1st lateral | 9.5 cm | 12 cm |
| 4th lateral | 12.5 cm | 16 cm |
| Spray formation | Inverted pyramid | Inverted pyramid |

It is claimed:

1. A new and distinct Chrysanthemum plant named Majesty, as described and illustrated.

* * * * *

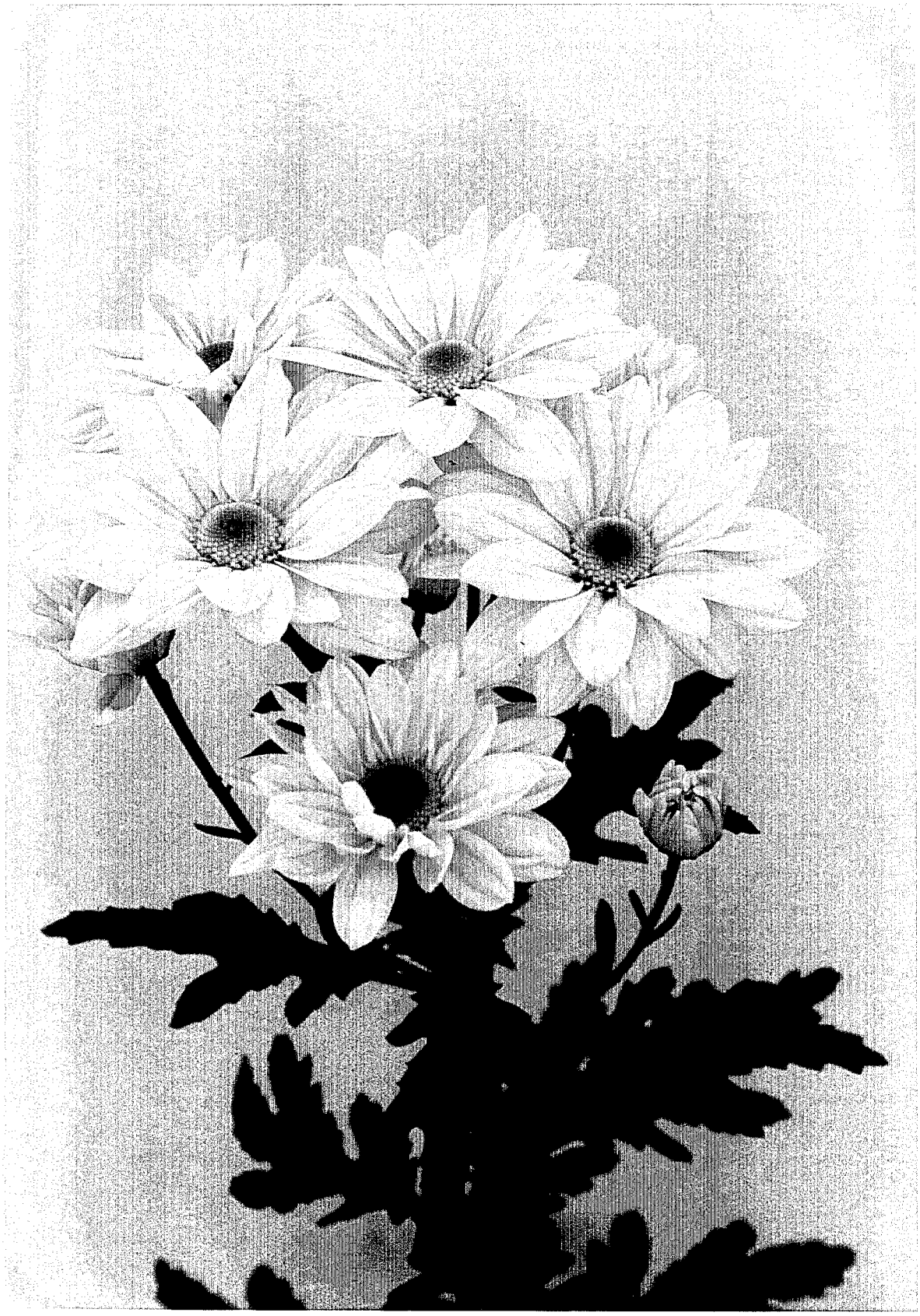

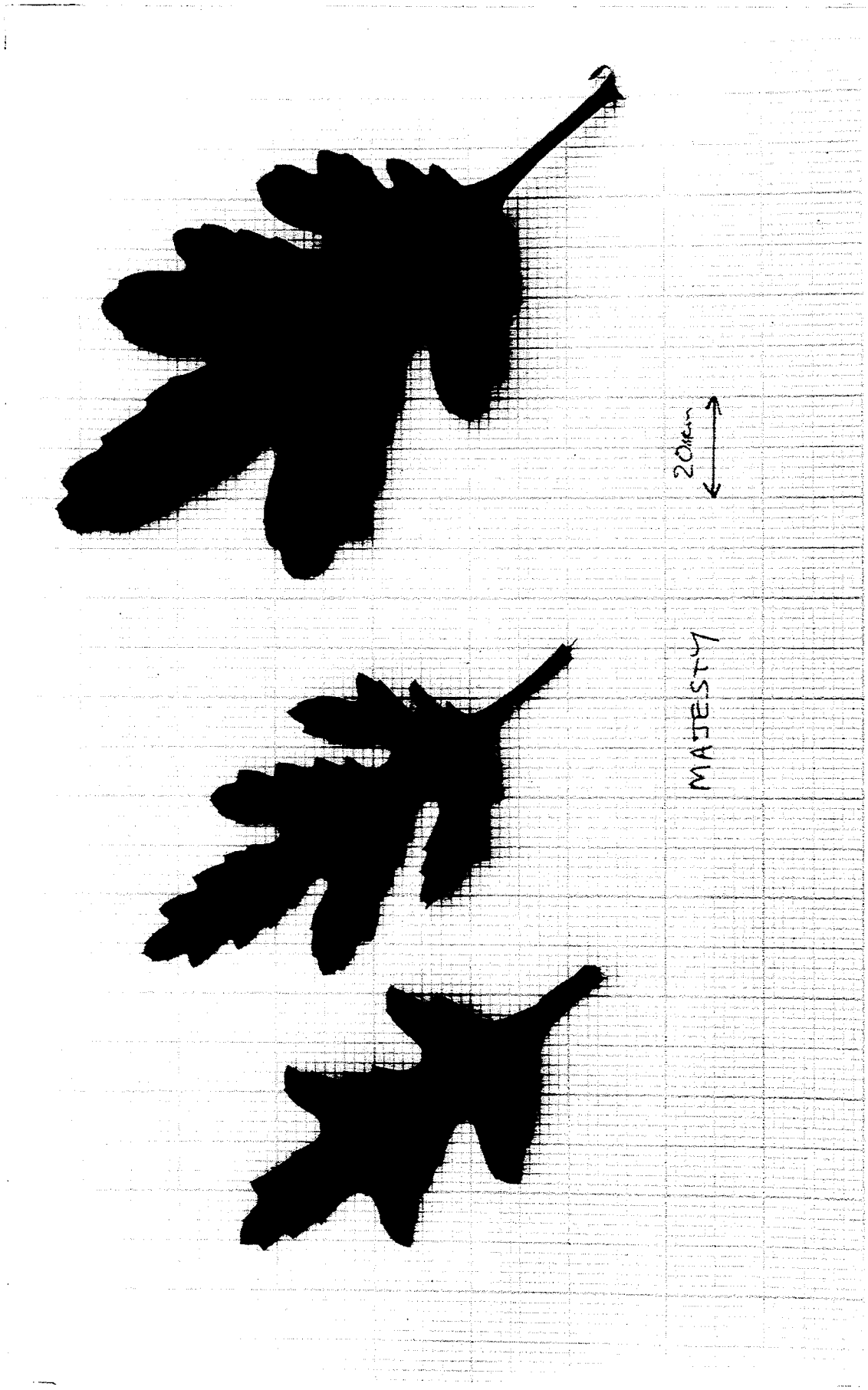
20cm
MAJESTY

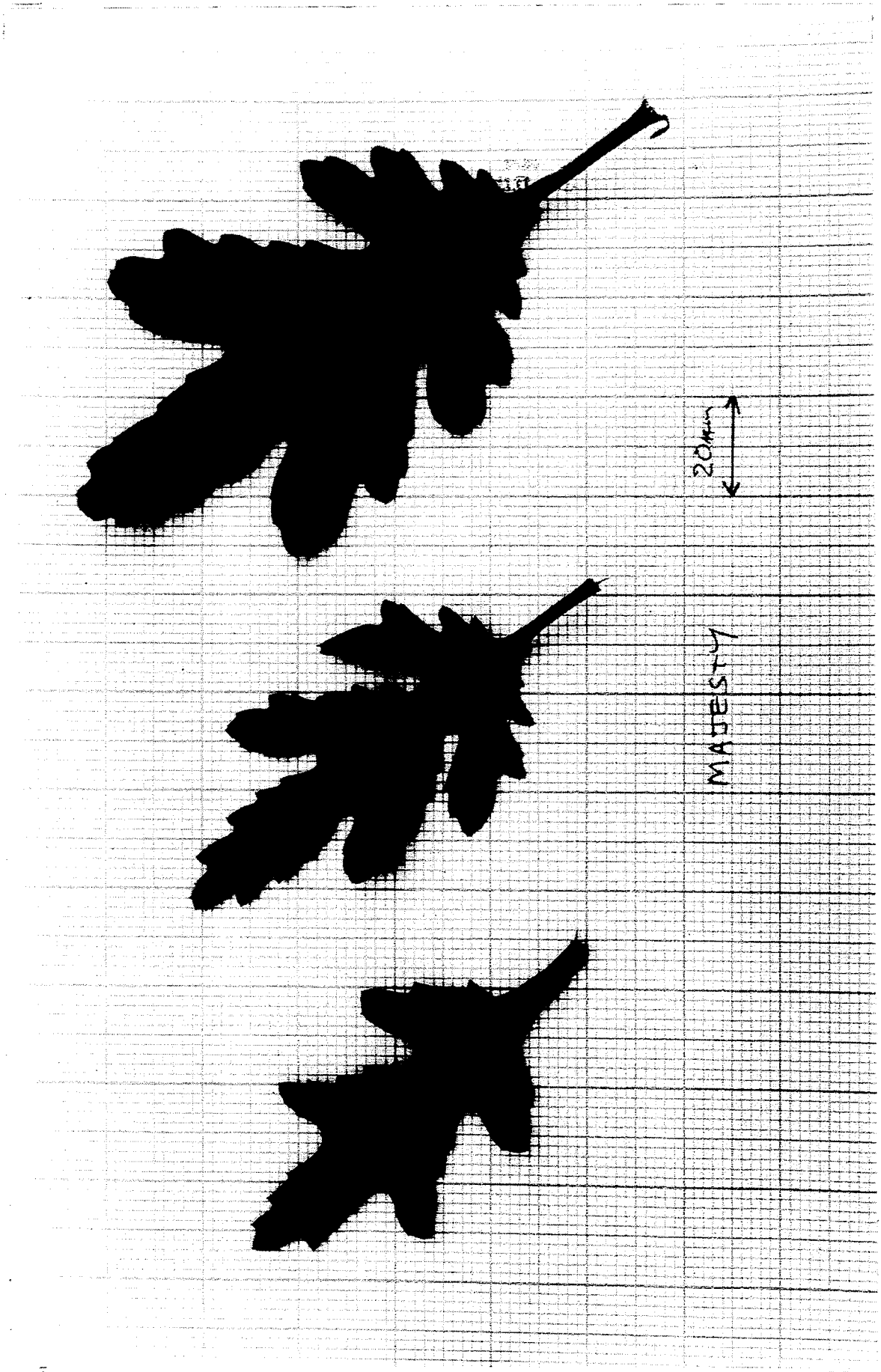
MAJESTY
20mm

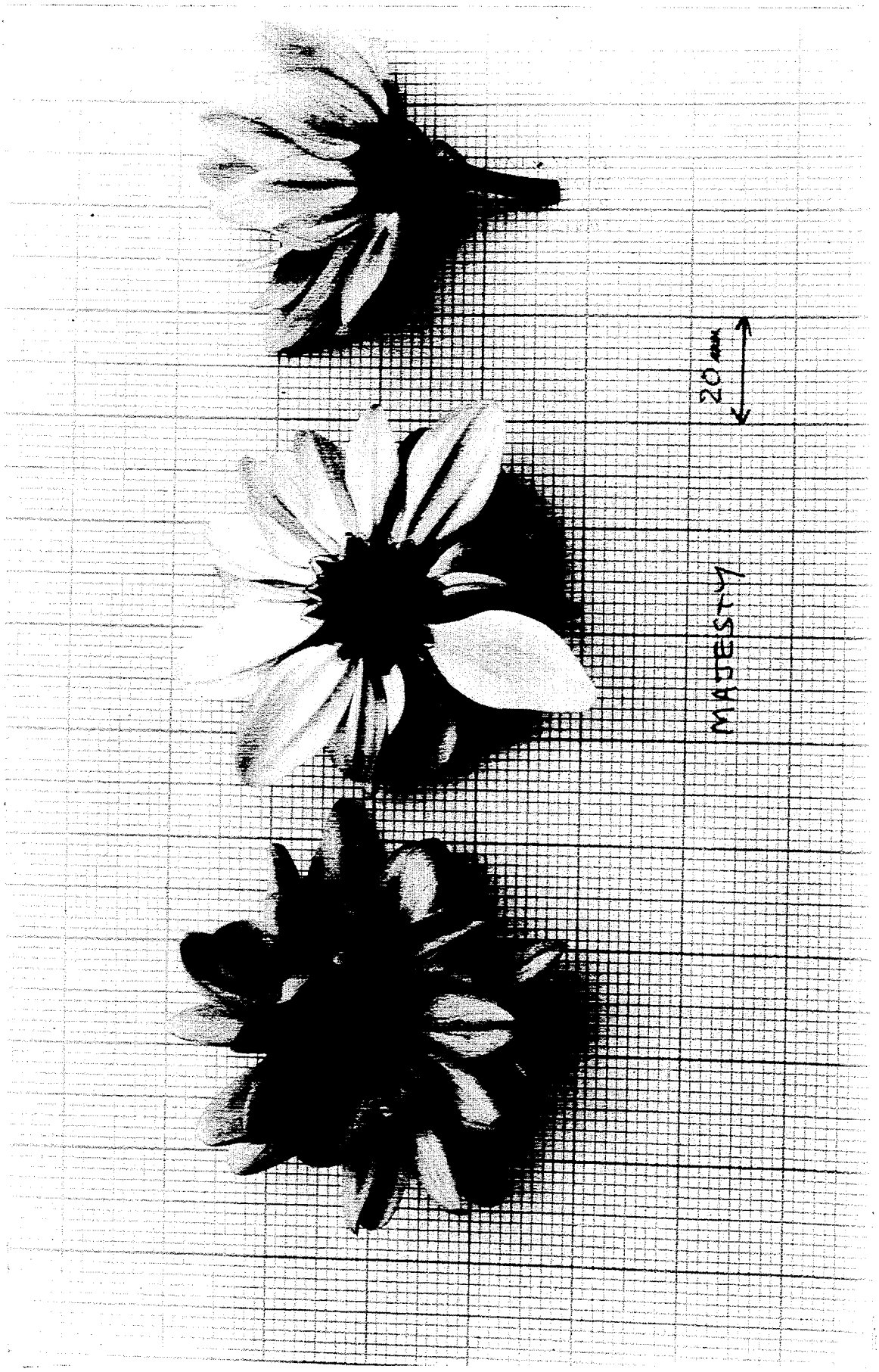
20 mm
MAJESTY